United States Patent
Hoepp et al.

[11] Patent Number: 5,892,129
[45] Date of Patent: Apr. 6, 1999

[54] PROCESS FOR THE PREPARATION OF 1,1, 3-TRIALKOXYPROPANE

[75] Inventors: Mathias Hoepp, Biebergemuend; Dietrich Arntz, Oberursel; Hans-Peter Ohlinger, Maintal; Willi Hofen, Rodenbach, all of Germany

[73] Assignee: Degussa Aktiengesellschaft, Frankfurt am Main, Germany

[21] Appl. No.: 859,845

[22] Filed: May 21, 1997

Related U.S. Application Data

[63] Continuation of Ser. No. 706,959, Sep. 3, 1996, abandoned, which is a continuation of Ser. No. 516,621, Aug. 18, 1995, abandoned.

[30] Foreign Application Priority Data

Sep. 8, 1994 [DE] Germany ............ 44 31 994.0

[51] Int. Cl.$^6$ .................................. C07C 43/30
[52] U.S. Cl. .................. 568/600; 568/605; 568/465; 568/460
[58] Field of Search .................. 568/465, 460, 568/600, 605

[56] References Cited

U.S. PATENT DOCUMENTS

| | | | |
|---|---|---|---|
| 2,288,211 | 6/1942 | Schulz | 260/602 |
| 2,800,513 | 7/1957 | Hall et al. | 568/600 |
| 3,317,613 | 5/1967 | Kunstle et al. | 568/605 |
| 4,024,159 | 5/1977 | Peterson | 568/603 |
| 4,374,999 | 2/1983 | Garrou | 549/453 |
| 4,536,585 | 8/1985 | Paparizos et al. | 549/453 |
| 4,579,979 | 4/1986 | Andrade et al. | 568/605 |
| 5,066,403 | 11/1991 | Dutta et al. | 210/638 |
| 5,216,179 | 6/1993 | Hoepp et al. | 549/372 |

FOREIGN PATENT DOCUMENTS

| | | |
|---|---|---|
| 1447211 | 7/1966 | France . |
| 1447138 | 12/1966 | France . |
| 898895 | 12/1953 | Germany . |
| 941974 | 4/1956 | Germany . |
| 957569 | 2/1957 | Germany . |
| 34 03 426 | 8/1985 | Germany . |
| 40 40 362 | 6/1992 | Germany . |
| 95/01949 | 1/1995 | WIPO . |

OTHER PUBLICATIONS

Ullmann's Encyclopedia of Industrial Chemistry, 5th Ed., vol. A 1 (1990), pp. 346–347.

Meskens, F.A.J., "Methods for the preparation of acetals from alcohols or oxiranes and carbonyl compounds", Synthesis (1981) pp. 501, 512, 513.

Ullmann's Encyclopedia of Industrial Chemistry, 5th Ed., vol. A 16 (1990), pp. 191–192 and 208.

Ullmann's Encyclopedia of Industrial Chemistry, 5th Ed., vol. A 9 (1990), p. 638.

Hall, R.H., et al., J. Chemical Society (1954), pp. 3388–3393.

Chemical Abstracts, vol. 45, col. 6571.

*Primary Examiner*—Margaret W. Glass
*Attorney, Agent, or Firm*—Beveridge, DeGrandi, Weilacher & Young, L.L.P.

[57] ABSTRACT

A process for the preparation of 1,1,3-trialkoxypropane by acid-catalyzed reaction of acrolein with a $C_1$ to $C_6$ alcohol, which can be carried out well on a large scale and leads to a higher selectivity. The process involves (a) the reaction, in the presence of a solid acid catalyst which is insoluble in the reaction mixture, (b) a partial neutralization of the reaction mixture, using an amine or basic ion exchanger, and (c) specific recovery by distillation of the reaction mixture and recirculation of fractions containing useful materials; aqueous fractions containing recyclable useful materials are largely dehydrated by pervaporation prior to being recirculated.

20 Claims, 1 Drawing Sheet

PROCESS FOR THE PREPARATION OF 1,1,3-TRIALKOXYPROPANE

This application is a continuation of application Ser. No. 08/706,959, filed Sep. 3, 1996, now abandoned, which is a continuation of Ser. No. 08/516,621 filed on Aug. 18, 1995, now abandoned, which application is entirely incorporated herein by reference.

INTRODUCTION AND BACKGROUND

The present invention relates to a process for the preparation of 1,1,3-trialkoxypropane by the acid-catalyzed reaction of acrolein with a lower alcohol. The process is particularly suitable for the continuous preparation of 1,1,3-trialkoxypropane with higher selectivity than previous methods.

The preparation of 1,1,3-trialkoxypropane by reaction of acrolein with a lower alcohol in the presence of hydrochloric acid or sulfuric acid as catalyst, partial or complete neutralization of the reaction mixture, and recovery of the same by distillation is known (see DE 898 895; R. H. Hall and E. S. Stern in J. Chem. Soc., 3388 to 3393 (1954)). In the acid-catalyzed reaction of acrolein (I) with a lower alcohol, not only is the desired 1,1,3-trialkoxypropane (IV) formed, but 3-alkoxypropionaldehyde (II) and acrolein dialkyl acetal (III) are also produced. As the following reaction scheme shows, equilibria exist between the above-mentioned substances (I) to (IV) in the presence of the acid catalyst:

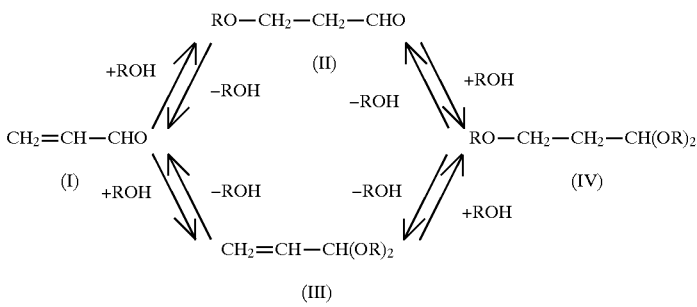

Owing to the complex equilibrium positions between the compounds (I) to (IV) and to the fact that further acrolein derivatives can be formed from acrolein and from the water arising during the formation of acetals, it has hitherto been difficult to obtain the desired 1,1,3-trialkoxypropane with higher selectivity and in higher total yield. In order as far as possible to avoid a reverse splitting of (IV) during the recovery of the reaction mixture by distillation, at least a partial neutralization of the reaction mixture prior to distillation is necessary. A disadvantage of the previously known process, in addition to the often unsatisfactory yield, is that the salts obtained in the reaction mixture from the neutralization of the catalyst lead to encrustations in the distillation equipment—encrustation of this kind is not acceptable in a large-scale plant.

According to DE 898 895 the equilibrium of the reaction can be shifted in favor of the desired trialkoxypropane by carrying out the reaction in the presence of substances which bind water. Such a measure is, however, very expensive on a commercial scale. DE 898 895 also includes instructions to azeotropically dehydrate, by means of benzene, the 3-methoxypropionaldehyde which forms as a by-product in Example 3 of DE 898 895 and is obtained mixed with water during recovery by distillation, and to add it to a subsequent batch. The disadvantage here is that a further organic solvent is necessary for the dehydration.

SUMMARY OF THE INVENTION

One object of the present invention is accordingly to provide an improved process for the preparation of 1,1,3-trialkoxypropane, which can be carried out without problems on a large scale and can be conducted batchwise or continuously.

Another object of the present invention is to obtain higher selectivity of 1,1,3-trialkoxypropane.

A still further object is to be able to feed the 3-alkoxypropionaldehyde formed as a by-product to a subsequent batch without the requirement for the concomitant use of a further organic solvent in order in this way to obtain a higher yield of 1,1,3-trialkoxypropane.

In achieving the above and other objects, one feature of the invention resides in the preparation of 1,1,3-trialkoxypropane by the reaction of acrolein with a $C_1$ to $C_6$ alcohol in the molar ratio of from 1 to greater than 3 at a temperature of from 10° to 100° C. in the presence of an acid catalyst to form a reaction mixture. This is then subjected to partial neutralization of the reaction mixture. A separation follows which is carried out by distillation of the partly neutralized reaction mixture.

In carrying out this reaction, (a) the process is carried out in the presence of a solid acid catalyst which is insoluble in the reaction mixture, (b) the pH value of the reaction mixture liberated from the catalyst is increased to 4.5 to 7, measured on a sample diluted with ten times the quantity of water, by addition of an amine or contact with a basic ion exchanger, and (c) the partly neutralized reaction mixture is separated by distillation into one or more low-boiling fractions substantially free of alkoxypropionaldehyde and an anhydrous high-boiling fraction. The latter contains 3-alkoxypropionaldehyde and 1,1,3-trialkoxypropane or, if the boiling points of water, of 3-alkoxypropionaldehyde and of the combined azeotropic mixture are close to one another, into a low-boiling fraction, a medium-boiling fraction containing essentially the entire quantity of 3-alkoxypropionaldehyde and water and a high-boiling fraction containing 1,1,3-trialkoxypropane. The 1,1,3-trialkoxypropane is distilled off from the high-boiling fraction in each case and the 3-alkoxypropionaldehyde distilled off from the high-boiling fraction or at least partly dehydrated by pervaporation from the medium-boiling fraction is fed to a subsequent batch.

BRIEF DESCRIPTION OF THE DRAWINGS

The present invention will be further understood with reference to the drawings wherein.

DETAILED DESCRIPTION OF THE INVENTION

Figure 1:
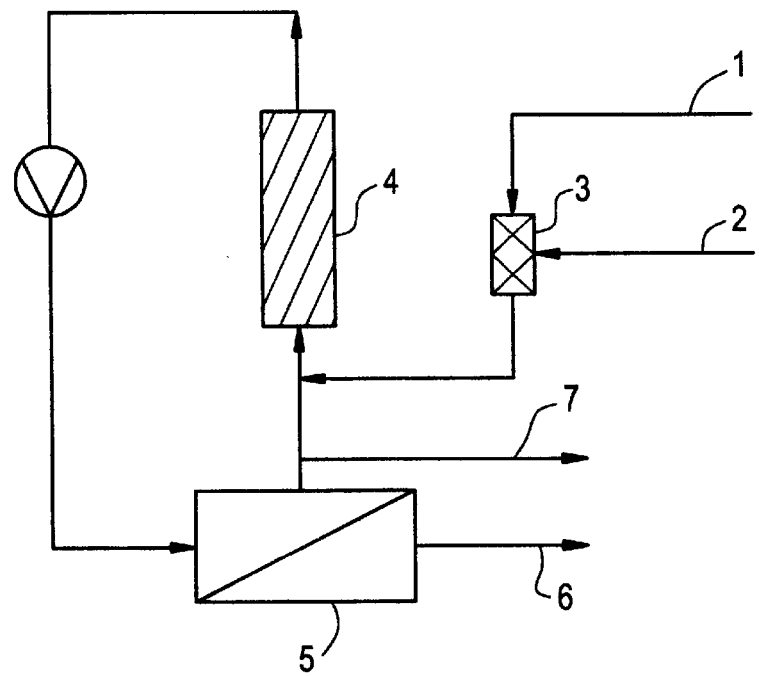
FIGS. 1 and 2 are, respectively, alternate flow diagrams illustrating the process of the invention.

The 1,1,3-trialkoxypropane to be prepared according to the method of the present invention contains three identical alkoxy groups having 1 to 6 C atoms, preferably 1 to 3 C atoms. Accordingly, alcohols having 1 to 6 C atoms, preferably 1 to 3 C atoms, are used in the preparation of 1,1,3-trialkoxypropane. The alcohols can be primary or secondary alcohols, but not tertiary alcohols. Linear alcohols having 1 to 3 C atoms, that is, methanol, ethanol and n-propanol, are preferably used, because the 1,1,3-trialkoxypropanes obtainable with these are suitable raw materials for the preparation of the corresponding 1,3-dialkoxypropanes which can be employed as solvents. 1,1, 3-triethoxypropane is particularly preferred.

To prepare 1,1,3-trialkoxypropane, acrolein and alcohol are used in a molar ratio of 1 to greater than 3, because an excess of alcohol shifts the equilibrium position in the desired direction; the upper limiting value for the molar ratio is in itself of little importance and will in general scarcely be above 1 to 20, so as not to render the process uneconomic. A molar ratio of acrolein to alcohol in the range of from 1 to 3.5 up to 1 to 10 and in particular from 1 to 4 up to 1 to 8 is preferred. It is advisable that the raw materials used be as free of water as possible, or that they contain only a low water content, because otherwise a less favorable establishment of equilibrium and increased formation of by-products result.

The reaction takes place in a temperature range of 10° and 100° C., preferably 30° and 70° C. At a reaction temperature in the region of the upper limit, the equilibrium is shifted more towards the feed materials and in addition there is an increased formation of by-products. At a very low temperature the velocity of the reaction may be too low for a sufficiently high production output to be achieved. The reaction is usually carried out at normal pressure; if desired, or if necessary at higher temperatures, a greater pressure can be applied.

The catalysts employed are solid acid catalysts which are insoluble in the reaction mixture. In particular inorganic and organic ion exchangers may be used. However, inorganic supporting materials having a high surface area, which contain a strong mineral acid sufficiently firmly adsorbed, can also be used—the acid should not in practice become separated from the catalyst surface during the reaction.

Of the organic ion exchangers, ion-exchange resins based on styrene/divinylbenzene copolymers containing sulphonate and phosphonate groups are particularly suitable, with strongly acidic sulphonate groups being preferred. It is advisable to use macroporous ion exchangers. The common commercially available perfluorinated sulfonic acid resins can also be used.

The preferred acidic inorganic ion exchangers are those based on polymeric organosiloxanes having sulphonate groups in accordance with DE 35 18 881 and DE 32 26 093 (respective English language equivalents are U.S. Pat. Nos. 4,647,644 and 4,552,700 which are incorporated by reference in their entirety), also acidic zeolites wherein the $SiO_2/Al_2O_3$ module is greater than 2, for example, Type Y zeolites, mordenite and ZSM 5, as well as layer silicates containing acidic intermediate layers, for instance montmorillonites pretreated with mineral acids.

After the equilibrium has been established, the reaction mixture formed according to the invention has a pH value, determined by the reaction, in the range generally of 3 to 6, mostly from 3 to 4.5, in each case measured when diluted with ten times the quantity of water. During recovery of the reaction, mixture, in order to avoid a reverse splitting of the 1,1,3-trialkoxypropane formed, the pH value must be increased first to a value of between 4.5 and 7, preferably of between 5.5 and 7, and particularly of between 6 and 7, in each case measured when diluted with ten times the quantity of water. As it is technically difficult to produce a pH value in the reaction mixture of exactly 7, while a pH value of above 7 must in any case be avoided, in practice a pH value of just under 7 is preferred. pH values of above 7 are to be avoided in the reaction mixture because otherwise spontaneous polymerization of the acrolein contained therein takes place. Provided the pH value of the reaction mixture at the conclusion of the reaction is 4.5 or more, increasing the pH can optionally be dispensed with. Preferably an amine, in particular a tertiary amine, is employed to increase the pH. Tertiary amines having a boiling point above the boiling point of the desired 1,1,3-trialkoxypropane are preferred as these high-boiling amines do not adversely affect the recovery of the reaction mixture by distillation and the return of individual fractions to a subsequent batch. Trialkanolamines are particularly suitable high-boiling tertiary amines. As an alternative to increasing the pH, the reaction mixture can be brought into contact with a basic ion exchanger, for example, a strongly basic organic ion exchanger.

The reaction mixture to be recovered by distillation consists essentially of 1,1,3-trialkoxypropane (IV), 3-alkoxypropionaldehyde (II), the corresponding alkanol and water. The term "essentially" means that the reaction mixture contains additional constituents, such as unreacted acrolein, acrolein dialkyl acetal (III), and by-products which are formed through Michael addition of one molecule of water to two molecules of acrolein and subsequent aldol condensation and acetalation. The composition of the reaction mixture depends on the selected molar ratio of acrolein to alkanol, on the water content of the educts used and the reaction temperature, and corresponds preferably to the respective equilibrium composition.

The process according to the invention can be carried out batchwise, for example, in a stirred-tank reactor, or continuously, for example, in a loop reactor, wherein the catalyst can be provided as a fixed bed or as a fluid bed. In principle all forms of reactors which ensure an adequate contact between the reaction mixture and the solid catalyst are suitable. Such forms of equipment are well known in the art.

In the batchwise reaction, it is preferable to place the alcohol in the reactor together with the acid catalyst and to add acrolein dropwise at the reaction temperature established. Following a further contact time the reaction mixture is cooled and the ion exchanger is filtered off. In the continuous process, acrolein and ethanol in the desired molar ratio are fed continuously to the reaction mixture and the corresponding quantity of reaction mixture is withdrawn for recovery. Raw materials recovered from recovery of the reaction mixture, such as acrolein and alcohol, and the acrolein by-products (III) and (II) are also usefully fed to the reaction mixture. For the contact time of the reaction mixture, expressed by the LHSV (liquid hourly space velocity) value, the value should be between 0.5 and 30 and preferably between 1 and 15.

In a preferred embodiment, the reaction is carried out in a circulating reactor (loop reactor, which has a container housing the catalyst bed, a circulation system and devices for introducing the reactants and withdrawing the reaction mixture; such equipment are well known in the art). In order to shift the equilibrium in the desired direction, it has proved to be of advantage to integrate into the circulation system a device for the partial dehydration of the reaction mixture. A pervaporation device is suitable for dehydrating the reaction mixture; with the use of a hydrophilic membrane, water permeates and the partly dehydrated reaction mixture remains on the side of the retentate. Equipment for the pervaporation and steps for carrying it out are known to the person skilled in the art—see Ullmann's Encyclopedia of Industrial Chemistry, 5th Ed., Vol. A 16 (1990), page 208 and Vol. A 9 (1987), page 638 and the references cited there. For a review of pervaporation, see Kirk-Other's *Encyclopedia of Chemical Technology,* (Third Edition), Volume 15, pages 92–131, especially pages 116–117; this excerpt is entirely incorporated herein by reference.

The procedure for the recovery by distillation of the previously at least partly neutralized reaction mixture depends on the boiling points of the 3-alkoxypropionaldehyde formed as a by-product and of its azeotropic mixture with water.

If the boiling points of water, of 3-alkoxypropionaldehyde and of the combined azeotropic mixture are close to one another, which is the case particularly with 3-methoxypropionaldehyde, the reaction mixture is separated into a low-boiling fraction containing unreacted acrolein and the excess alcohol, a medium-boiling fraction containing essentially the entire quantity of 3-alkoxypropionaldehyde and the entire quantity of water, and a high-boiling fraction containing the desired 1,1,3-trialkoxypropane and high-boiling by-products. Since 1,1,3-trialkoxypropane can also be decomposed again thermally in the presence of water, the separation of the medium-boiling fraction should be carried out as rapidly as possible and under mild conditions. 1,1,3-trialkoxypropane is distilled off from the high-boiling fraction. For the purpose of returning the 3-alkoxypropionaldehyde to a subsequent batch, the aqueous medium-boiling fraction is at least partly dehydrated using a pervaporation device with a hydrophilic membrane.

In the preparation of a 1,1,3-trialkoxypropane in which the alkoxy groups have two or more than two carbon atoms, it has proved to be particularly useful to separate the reaction mixture by distillation in such a way that first of all one, optionally several, low-boiling fractions substantially free of alkoxypropionaldehyde and containing the main components acrolein, alcohol and water, is or are separated and 3-alkoxypropionaldehyde and 1,1,3-trialkoxypropane are distilled off from the remaining anhydrous high-boiling fraction. In the preparation of triethoxypropane it is advantageous to remove all the low-boiling constituents in one fraction; the low-boiling fraction contains in addition the acrolein diethyl acetal which is present as a by-product in the equilibrium system.

Prior to the reintroduction of the useful materials acrolein and alcohol contained in the aqueous low-boiling mixture, part of the water must be removed. This can be effected by distillation wherein, however, in the case of an ethanolic low-boiling mixture, a residual water content of about 4% remains in the distillate owing to the formation of the azeotropic mixture of ethanol and water; whereas the distillate can be recycled, the aqueous material at the bottom of the column, which contains also acrolein diethyl acetal, must be removed.

It was then surprisingly found that aqueous low-boiling mixtures can be dehydrated advantageously by pervaporation to a residual water content of less than 1%. Here the low-boiling mixture is passed across a hydrophilic membrane at a temperature of from 40° to 105° C., advantageously at 60° to 100° C., and the permeating substance is withdrawn in gaseous form at a pressure of from 0.1 to 50 mbar, advantageously at 1 to 30 mbar. For this, as also for the pervaporation measures already mentioned above, all kinds of well known hydrophilic membranes can be employed, such as, for example, polyvinyl alcohol membranes or symplex composite membranes. An important advantage of the dehydration by pervaporation of aqueous low-boiling mixtures and also of aqueous medium-boiling mixtures is that neither a further organic solvent for the purpose of azeotropic dehydration nor a drying agent is necessary. Another advantage is that the acrolein dialkyl acetal which may be contained in a low-boiling fraction is not lost during dehydration by pervaporation, but can be recycled with the dehydrated low-boiling fraction together with the alcohol and unreacted acrolein. This increases the yield and reduces the costs of disposal.

The process according to the invention can be carried out batchwise and continuously on a large scale, surprisingly without leading to encrustations in the distillation equipment. Only very small quantities of neutralizing agents are required, as the solid acid catalysts are insoluble in the reaction medium. When the preferred tertiary amines are used as neutralizing agents, the ammonium salts which form remain in non-crystalline form in the bottom of the distillation column during recovery of the reaction mixture.

Surprisingly, the selectivity of 1,1,3-trialkoxypropane and in particular of 1,1,3-triethoxypropane could be significantly increased by the method of separating the reaction mixture by distillation. Finally, a further advantage to be emphasized is the simple dehydration of aqueous fractions from the recovery of the reaction mixture and the return of the at least partly dehydrated phases to the subsequent reaction batch. The equilibrium can in addition be shifted by the integration of a pervaporation stage in a loop reactor, so that the reaction mixture withdrawn from circulation has a higher content of 1,1,3-trialkoxypropane and the quantity of the components to be returned can be decreased; operating and plant costs are thereby lowered.

FIG. 1 shows a flow diagram for carrying out the process of the invention wherein acrolein (1) is introduced into a static mixture (3) which is also charged with alcohol (2). The mixture flows to a fixed bed reactor (4) and then to a pervaporation unit (5). The permeate exits (6) and the reaction mixture is then obtained (7).

Figure 2:
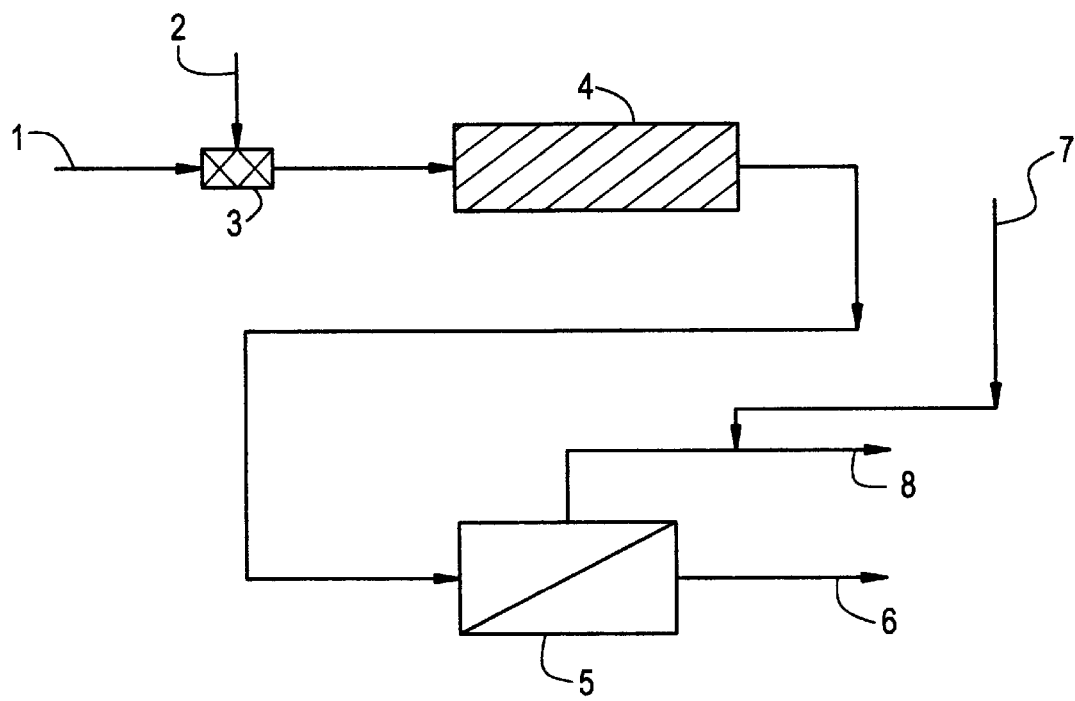

In FIG. 2 acrolein (1) is charged to static mixture (3) and alcohol (2) is also introduced. The fixed bed reactor (4) is the site of the reaction and the reaction mixture flows to pervaporation unit (5). A neutralizing agent is introduced (7) into the line for the distillation product (8). The permeate is then recovered at (6).

The following examples are illustrative of the invention:

EXAMPLE 1

1150 g of absolute ethanol and 40 g of strongly acidic ion-exchange resin (Amberlyst® 15 from the firm Rohm & Haas) are placed in a reactor and heated to 50° C. 292 g of acrolein (96%) are added within 30 minutes, with the internal temperature being maintained in the range of from 50° to 53° C. After addition is complete, stirring is continued for 4 hours at an internal temperature of 50° C. Stirring is then continued for a further 2 hours at 20° C. The ion-exchange resin is filtered off and an ethanolic solution of triethanolamine is added to the reaction mixture until a sample of the reaction mixture has a pH value of greater than 6 and less than 7 after tenfold dilution with water.

The reaction mixture is recovered by distillation, whereby a low-boiling mixture of ethanol, water, acrolein and acrolein diethyl acetal is first of all distilled off at a temperature of 67° to 79° C. at the head and a pressure of 1000 mbar, using a 70 cm column filled with wire mesh rings. Subsequently, 120 g of 3-ethoxypropionaldehyde (II) (23%) is distilled off first from the remaining high-boiling fraction at 65° to 68° C. and 88 mbar, and then 585 g of 1,1,3-triethoxypropane (IV) (67%) is distilled off at 92° to 94° C. and 50 mbar.

EXAMPLE 2

(a) The reaction is carried out as in Example 1, but ethanol having a water content of 4% is used. Owing to the worsened equilibrium position compared with Example 1 and the increased formation of by-products, recovery by distillation, performed as in Example 1, produced 130 g of 3-ethoxypropionaldehyde (25%) and 440 g of 1,1,3-triethoxypropane (50%).

(b) Recovery not according to the invention: The reaction is carried out as in Example 2a. The reaction mixture is distilled via an efficient separating column having 15 theoretical trays. First of all a low-boiling mixture having a water content of 4.8% is distilled off at 78° C. and 1000 mbar, then a mixture of water and 3-ethoxypropionaldehyde is distilled off at 43° C. and 100 mbar and finally 1,1,3-triethoxypropane is distilled off at 101° C. and 50 mbar. (The azeotropic mixture of ethoxypropionaldehyde and water (42.5% of $H_2O$) boils at 93° C. at normal pressure.) 102 g of 3-ethoxypropionaldehyde (20%) is obtained, present as a mixture with water, and 302 g of 1,1,3-triethoxypropane (35%). The proportion of acrolein in the low-boiling mixture is 5.0%, whereas in Example 2a it was only 1.5%. The latter and the reduced yield are evidence of a decomposition during the distillation.

EXAMPLE 3

The reaction and the recovery by distillation are carried out as in Example 1. The low-boiling mixture separated off has a mass of 686 g and is of the following composition: 0.6% of acrolein, 10.2% of water, 87.6% of ethanol and 1.6% of acrolein diethyl acetal (III).

This mixture is pumped at a volumetric flow rate of 100 1/h across 100 $cm^2$ of a membrane (Pervap® 1000 from the firm Deutsche Carbone). The operation is carried out batchwise at a temperature of 80° C. and a pressure of the permeating substance of 10 mbar. The permeating substance is condensed using liquid nitrogen. After an operating time of 10 hours, there are obtained 84 g of the permeating substance having a water content of 73% (26% of EtOH), and 584 g of retentate having a water content of 0.5%, 0.7% of acrolein, 97% of ethanol and 1.7% of (III).

A conversion of 98.5% is obtained for acrolein and of 50.7% for ethanol, with reference to the feed materials. The selectivity with regard to (IV) is 67.5% for acrolein, 78.7% for ethanol. The total selectivity with regard to (IV), (II) and (III) is 93.0% for acrolein, 89% for ethanol. If the reuse of (II) and (III) in subsequent batches is taken into account, in a continuous process a selectivity with regard to (IV) of 90% is obtained for acrolein and 88% for ethanol.

EXAMPLE 4

The following quantities per hour were reacted and recovered in a continuously operated experimental plant containing a fixed bed reactor:

1235 g of acrolein (96%) and 2865 g of ethanol are pumped into a premixer, together with 5455 g of the retentate from the pervaporation stage (5380 g of ethanol, 25 g of water, 20 g of ADEA (acrolein diethyl acetal) (III) and 30 g of acrolein) and 430 g of EPA (ethoxypropionaldehyde) (II) from the second distillation stage. This mixture is pumped continuously at 50° C. over a fixed catalyst bed containing 2000 g of strongly acidic cation-exchange resin (Amberlyst® 15). For the purpose of neutralization, 40 g of a 50% solution of triethanolamine in ethanol is pumped continuously into the reaction mixture running off.

The neutralized reaction mixture is liberated from the low-boiling constituents in a first distillation column at normal pressure. 5840 g of distillate (5400 g of EtOH, 390 g of water, 20 g of ADEA and 30 g of acrolein) and 4055 g of residue (430 g of EPA, 3280 g of TREP (triethoxypropane) (IV), 345 g of high-boiling constituents) are obtained.

The distillate is heated to 100° C., fed to a pervaporation unit and there dehydrated. The membrane surface is 1 $m^2$ of Pervap® 1516. The permeating substance is condensed at −20° C. using cooling salt water. 485 g of the permeating substance (365 g of water, 120 g EtOH) and 5355 g of retentate are obtained per hour; the latter is returned to the reaction in the premixer.

The residue from the first distillation is subjected to a second distillation at 100 mbar. Here 430 g of EPA is distilled off and is also returned to the premixer. The residue from the second distillation is again distilled at 50 mbar, with 3280 g of 1,1,3-triethoxypropane being obtained.

The selectivity with regard to TREP is 88% for acrolein and 89.8% for ethanol.

EXAMPLE 5

800 g of methanol and 30 g of acidic ion-exchange resin (Amberlyst® 15) are placed in a reactor and heated to 50° C. 292 g of acrolein (96%) are added within 30 minutes, with the internal temperature being maintained in the range of from 50° to 53° C. After addition is complete, stirring is continued for 4 hours at an internal temperature of 50° C. The reaction mixture is then cooled, the ion-exchange resin is filtered off and a methanolic solution of triethanolamine is added to the reaction mixture until the latter has a pH value of 6.5 after tenfold dilution with water.

The reaction mixture is separated into its components by distillation. Unreacted acrolein (8 g) and methanol (380 g) are distilled off in the first fraction; these can be reused directly for the next batch. A mixture of water (76 g) and methoxypropionaldehyde (85 g) together with some methanol (15 g) and trimethoxypropane (17 g) are distilled off in the second fraction. The third fraction contains 465 g of pure trimethoxypropane.

The entire 193 g of the second fraction is pumped at a volumetric flow rate of 100 1/h across 100 $cm^2$ of a membrane (Pervap® 1000 from the firm Deutsche Carbone). The operation is carried out batchwise at a temperature of 80° C. and a pressure of the permeating substance of 10 mbar. The permeating substance is; condensed using liquid nitrogen. After an operating time of 10 hours, there are obtained 92 g of the permeating substance containing 82% of water and 15% of methanol and 97 g of retentate having a water content of 0.5%, 83% of methoxypropionaldehyde and 16% of trimethoxypropane. The retentate can be reused for the next reaction.

A conversion of 97% is obtained for acrolein and of 52% for methanol, with reference to the feed materials. If the reuse of the retentate and of the first fraction is taken into account, in a continuous process a selectivity with regard to trimethoxypropane of 91% is obtained for acrolein and 88% for methanol.

Further variations and modifications of the foregoing will be apparent to those skilled in the art and such variations and modifications are intended to be encompassed by the claims that are appended hereto.

German Priority Application P 44 31 994.0 filed on 8 Sep. 1994 is relied on and incorporated by reference in its entirety.

We claim:

1. A process for the preparation of 1,1,3-trialkoxypropane, said process comprising mixing acrolein with a $C_1$ to $C_6$ primary alcohol to form a reaction mixture, wherein the molar ratio of acrolein: alcohol is 1: greater than 3, reacting said reaction mixture at a temperature of from 10° C. to 100° C. in the presence of a solid acid catalyst which is insoluble in said reaction mixture; carrying out a neutralization of said reaction mixture by adding an amine or a basic ion exchanger, which is a styrene/divinylbenzene copolymer containing sulphate and phosphate groups to form a reaction mixture to obtain a pH value of 4.5 to 7 of said reaction mixture liberated from said catalyst, measured on a sample of reaction mixture diluted with ten times the quantity of water; and (i) separating by distillation said reaction mixture into one or more low-boiling fractions substantially free of alkoxypropionaldehyde and an anhydrous high-boiling fraction containing 3-alkoxypropionaldehyde and 1,1,3-trialkoxypropane, and distilling off said 1,1,3-trialkoxypropane from said high-boiling fraction and distilling off said 3-alkoxypropionaldehyde from said high-boiling fraction, or (ii) separating by distillation said reaction mixture into a low-boiling fraction, a medium-boiling fraction containing essentially all of said 3-alkoxypropionaldehyde and water, and a high boiling fraction containing 1,1,3-trialkoxypropane, distilling off said 1,1,3-trialkoxypropane from said high-boiling fraction or at least partly dehydrating said 3-alkoxypropionaldehyde by pervaporation from said medium-boiling fraction, and feeding said 3-alkoxypropionaldehyde to a subsequent batch.

2. The process according to claim 1, wherein said 1,1,3-trialkoxypropane contains three identical alkoxy groups having 1 to 6 carbon atoms.

3. The process according to claim 1, wherein said 1,1,3-trialkoxypropane contains three identical alkoxy groups having 1 to 3 carbon atoms.

4. The process according to claim 1, wherein said alcohol has 1 to 3 carbon atoms.

5. The process according to claim 1, wherein said alcohol is methanol, ethanol or n-propanol.

6. The process according to claim 1, wherein said molar ratio of said acrolein to said alcohol is no greater than 1:20.

7. The process according to claim 6, wherein said molar ratio of said acrolein to said alcohol is 1:3.5 to 10.

8. The process according to claim 7, wherein said molar ratio of said acrolein to said alcohol is 1:4 to 8.

9. The process according to claim 1, wherein said temperature is from 30° to 70° C.

10. The process according to claim 1, wherein said pH is from 5.5 to 7.

11. The process according to claim 1, wherein said pH is from 6 to 7.

12. The process according to claim 1, wherein said amine is a tertiary amine.

13. The process according to claim 1, wherein said amine has a boiling point above the boiling point of 1,1,3-trialkoxypropane.

14. The process according to claim 1, wherein said process is a batch process in which said acrolein is added dropwise to said alcohol and said catalyst.

15. The process according to claim 1, wherein said process is a continuous process having a liquid hourly space velocity of between 0.5 to 30.

16. The process according to claim 15, wherein said liquid hourly space velocity is between 1 to 15.

17. The process according to claim 1, wherein said acrolein and said alcohol are fed continuously to said reaction mixture.

18. The process according to claim 1, further comprising partially dehydrating said reaction mixture by pervaporation prior to the neutralization.

19. The process according to claim 1, further comprising dehydrating said low boiling fraction containing water and/or said medium boiling fraction containing water by pervaporation at a temperature of from 40° to 105° C. to a residual water content of less than 1%.

20. The process according to claim 18, wherein dehydrating the reaction mixture is carried out at a temperature of 60° to 100° C.

* * * * *